United States Patent [19]

Nosco et al.

[11] 4,152,390
[45] May 1, 1979

[54] CHEMICAL ANALYZER

[75] Inventors: Louis C. Nosco, Rochester; Henry S. Adamski, Webster; Anthony P. Di Fulvio, Rochester, all of N.Y.

[73] Assignee: Eastman Kodak Company, Rochester, N.Y.

[21] Appl. No.: 856,834

[22] Filed: Dec. 2, 1977

Related U.S. Application Data

[63] Continuation of Ser. No. 751,912, Dec. 17, 1976, abandoned.

[51] Int. Cl.² .................... G01N 33/16; G01N 21/24
[52] U.S. Cl. .................................. 422/63; 422/57; 422/58; 422/61; 422/65
[58] Field of Search ................. 23/230 R, 253 R, 259

[56] References Cited

U.S. PATENT DOCUMENTS

| | | | |
|---|---|---|---|
| 3,533,744 | 10/1970 | Unger | 23/253 R |
| 3,574,064 | 4/1971 | Binnings et al. | 23/253 X |
| 3,904,372 | 9/1975 | Lightner | 23/253 R |

Primary Examiner—R. E. Serwin
Attorney, Agent, or Firm—D. D. Schaper

[57] ABSTRACT

A chemical analyzer is disclosed for performing analysis on selected fluids. The analyzer comprises a plurality of cartridges containing test slides. A slide transfer mechanism is adapted to feed a slide from a selected cartridge, transport the slide to a metering device where a precise amount of fluid is deposited thereon, deliver the slide to conveyor means which moves the element through an incubator, and transport the slide to an analysis means after a predetermined time in the incubator.

20 Claims, 5 Drawing Figures

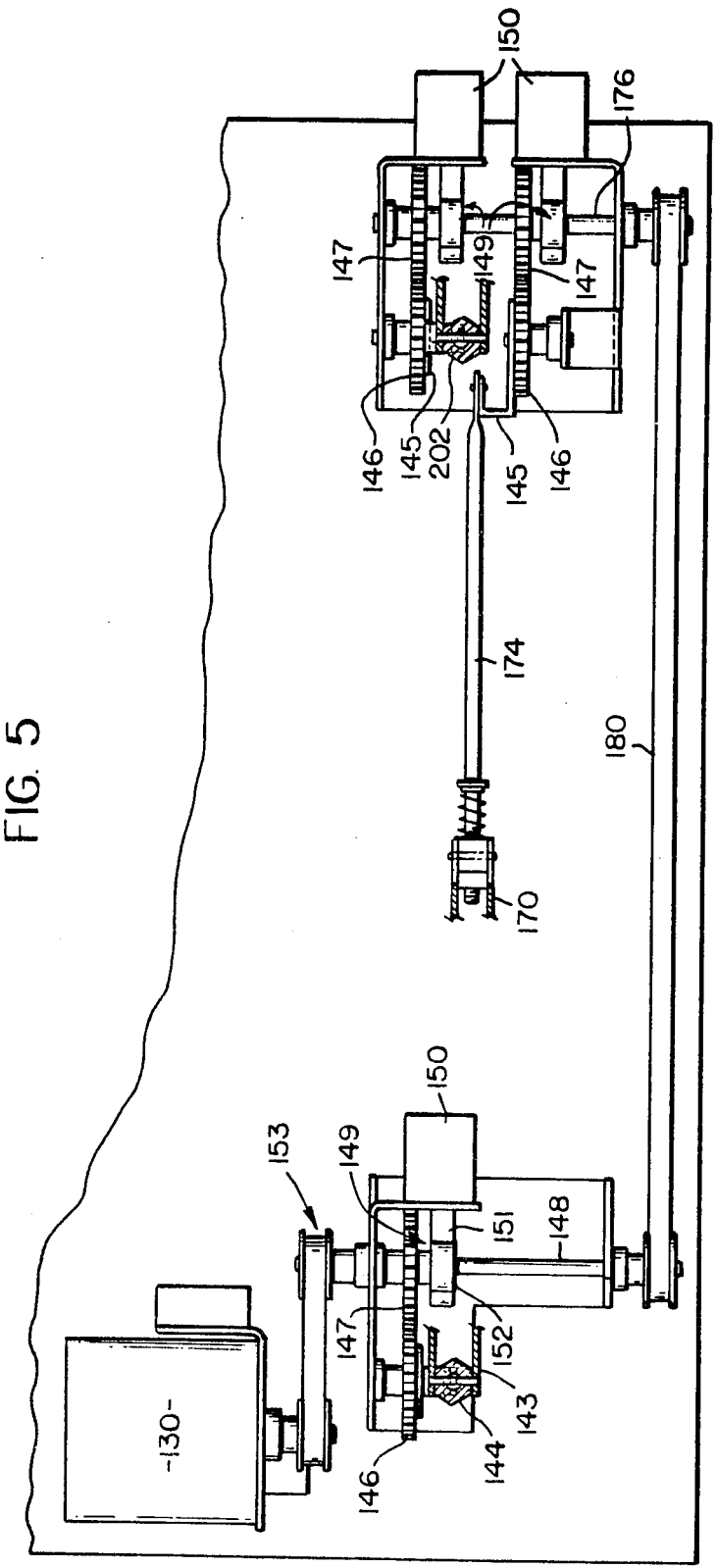

4,152,390

CHEMICAL ANALYZER

CROSS-REFERENCES TO RELATED APPLICATIONS

This application is a continuation of copending application Ser. No. 751,912, filed Dec. 17, 1976, now abandoned.

Reference is made to commonly-assigned U.S. Patent Applications: Ser. No. 644,014, entitled GAS PRESSURE-DROP DISPENSER, filed in the name of Richard L. Columbus, on Dec. 24, 1975, and now U.S. Pat. No. 4,041,995; and Ser. No. 857,344, entitled METHOD AND APPARATUS FOR CHEMICAL ANALYSIS, filed in the name of Glover et al on Dec. 5, 1977.

BACKGROUND OF THE INVENTION (1) Field of the Invention

This invention relates to the chemical analysis of substances, and more particularly, to apparatus for the automatic analysis of biological fluids.

(2) State of the Prior Art

In recent years, a number of automated systems have been developed for carrying out quantitative chemical analyses of fluid samples. Most of the commercially-available systems utilize liquid reagents and require analyzer equipment having intricate solution handling and transport capabilities. One widely used system, shown in U.S. Pat. No. 2,797,149, employs a continuous-flow technique in which successive samples are separated from one another by immiscible fluid segments such as gas or air bubbles. Such a system is complex and expensive, requires skilled operators, and necessitates a considerable expenditure of time and effort in repetitive cleaning operations.

Another liquid analysis system is disclosed in U.S. Pat. No. 3,788,816, in which a turntable carries a plurality of receptacles containing samples to be analyzed and a plurality of tube modules which are adapted to receive preset volumes of sample and reagent. Coaxially disposed relative to the turntable is a vertically movable rotary element comprising a probe tip which serves to dispense reagents and to transfer sample to a spectrophotometer.

U.S. Pat. No. 3,883,308, to Matte, discloses liquid analysis apparatus in which a plurality of sample containers are carried on a circular support, a plurality of reagent cups are supported on a second circular support, and an aspirator is provided for transferring fluid from a sample container to a selected reagent cup. The bottom portions of the reagent cups are transparent to facilitate a photometric reading through the container.

As an alternative to liquid analysis systems, various essentially-dry analytical elements have been adopted for automated test procedures. Although these elements offer substantial storage and handling conveniences, compared to "wet-chemistry," they have enjoyed only limited success and have been used primarily for qualitative and semi-quantitative test purposes. Apparatus for use with analytical elements in the form of continuous webs is shown in U.S. Pat. Nos. 3,036,893, and 3,526,480. Since the reagents are contained on the web in a predetermined sequence, the versatility of this apparatus is quite limited.

Automatic slide handling apparatus is known in clinical apparatus of the "wet-chemistry" type. In one such apparatus, shown in U.S. Pat. No. 3,574,064, glass slides are fed from a single supply station onto a turntable. Slides carried on the turntable are moved past a metering station, and then through wash and incubation stations spaced around the periphery of the turntable. Slides processed by the apparatus are ejected from the turntable into a slide receiver adjacent the slide supply station. There is no provision for automatic analysis of the processed slides, and they must be manually removed from the slide receiver for examination under a laboratory microscope.

U.S. Pat. No. 3,904,372, discloses apparatus for handling chromatographic plates in which plates are removed from a supply magazine by a pick-up arm, placed in position for spotting with an aliquot of fluid, and then transferred by the pick-up arm to a liquid development tank. The pick-up arm is pivotally mounted and utilizes a vacuum means to grip and hold the plates as they are transferred from the magazine to the development tank.

U.S. Pat. No. 3,533,744, discloses apparatus in which generally rectangular, flat sample containers are loaded onto an endless belt. As the sample containers are moved through the apparatus, liquid reagents are added to the containers; the containers are then moved past an analytical means prior to being conveyed to a disposal bin.

In apparatus, such as that described above in U.S. Pat. No. 3,574,064, U.S. Pat. No. 3,904,372, and U.S. Pat. No. 3,533,744, the apparatus work stations are spaced apart, and slide carriers employing relatively complex slide holding mechanisms must be used to move a slide from station to station. Further, in the use of slide carriers, such as turntables and endless belts, all slides must move through the various work stations at the same speed. Thus, the rate at which slides can be processed is determined by the slowest operation to be performed.

U.S. Pat. No. 2,904,914, to Trubert discloses a lantern-slide carrier comprising a movable driver plate which is formed with a pair of flexible tongues. As the driver plate is manually reciprocated, one of the tongues moves a first slide from a magazine into a viewing position while the other tongue moves a second slide from the viewing position to a storage container. There is no suggestion that such a slide carrier could be used in clinical apparatus.

OBJECTS OF THE INVENTION

It is an object of the invention to provide apparatus for analyzing biological fluid in which a test slide can be slideably advanced through the apparatus along a path formed by elements of the apparatus.

A further object of the invention is to provide apparatus for analyzing biological fluid in which fluid is metered onto discrete test slides which are advanced through the apparatus by a plurality of reciprocatively mounted, independently actuatable drive means.

Another object of the invention is to provide a slide transfer mechanism for an analyzer of the type described in which a plurality of independently actuatable drive means can be selectively engaged with a single power source.

Other objects and advantages will become apparent from the following Summary and Description of the Preferred Embodiment, when considered in the light of the attached drawings.

SUMMARY OF THE INVENTION

This invention relates to apparatus for the automatic continuous analysis of biological fluids in which a fluid sample is metered onto a test slide which is analyzed after an appropriate period of incubation. More specifically, the invention is directed to apparatus comprising a plurality of elements adapted to interact with a test slide in a preselected sequence, the elements including metering means for depositing a predetermined quantity of sample on a slide in a metering position and analysis means for sensing a characteristic of the slide after a predetermined period of time. A slide path is provided for movement of slides between the elements, the path being adapted to support slides in contact therewith for slidable movement thereon. A slide handling means is adapted to sequentially apply a force to a slide supported on the path to advance the slide past the elements.

The slide handling means preferably includes a plurality of independently actuatable drive means which are mounted for reciprocation. The drive means are adapted to engage a slide in a predetermined sequence to advance the slide through the analyzer, and each of the drive means can be selectively engaged with a single power source.

The invention is particularly suitable for use in performing analyses of blood sera in which the serum is dispensed onto a test element, or a test slide, of the type which is formed as a multi-layer element containing the necessary reagents for reaction with components of the serum. However, the invention is not limited to use with just such test slides, nor is it limited to just the analysis of blood sera, and other fluids can be used with apparatus of the type disclosed.

BRIEF DESCRIPTION OF THE DRAWINGS

FIG. 5 is a sectional view, taken along the line 5—5 in FIG. 3.

DESCRIPTION OF THE PREFERRED EMBODIMENT

Figure 1:
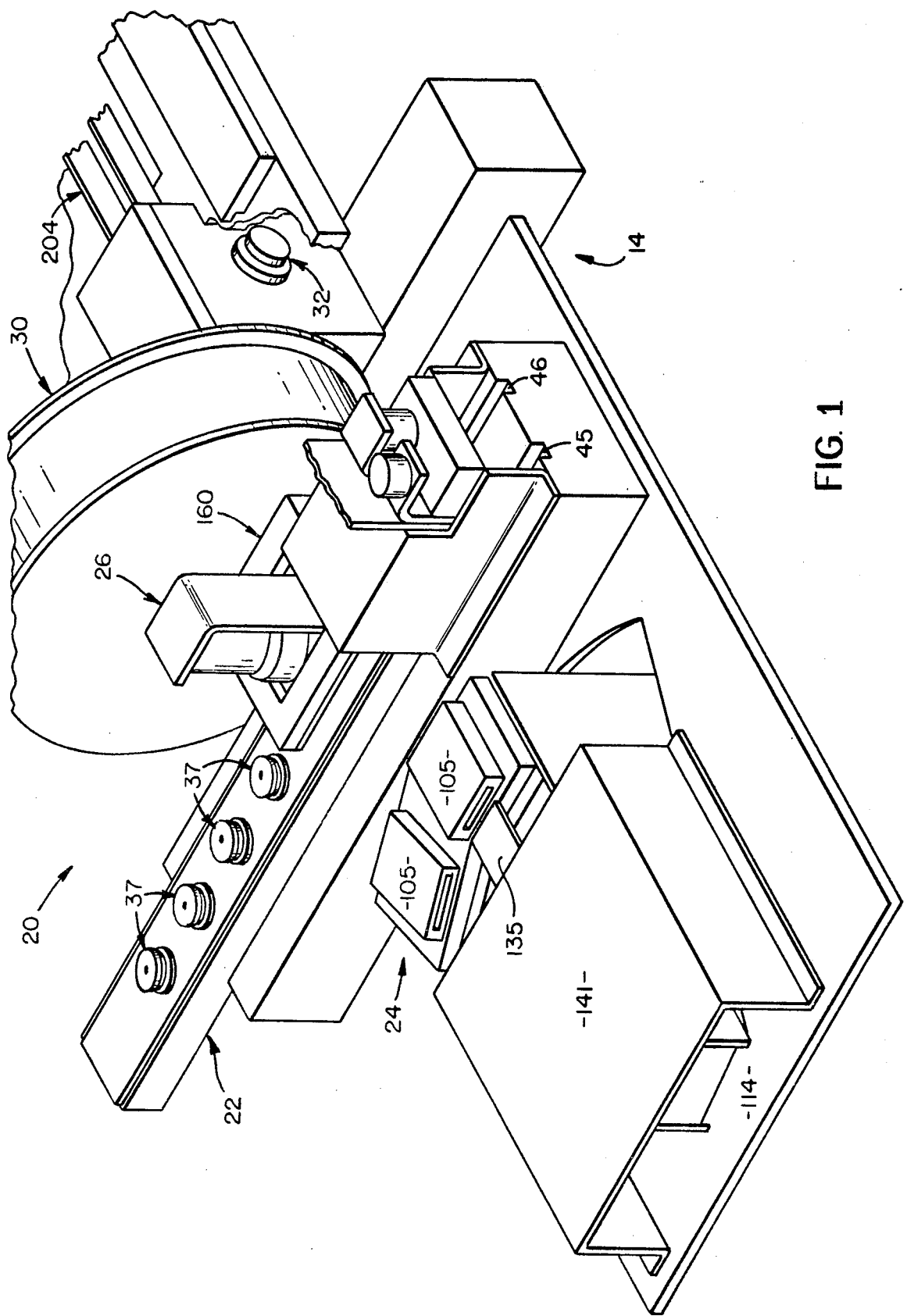
FIG. 1 is a perspective view of an analyzer constructed in accordance with the invention.
Figure 2:
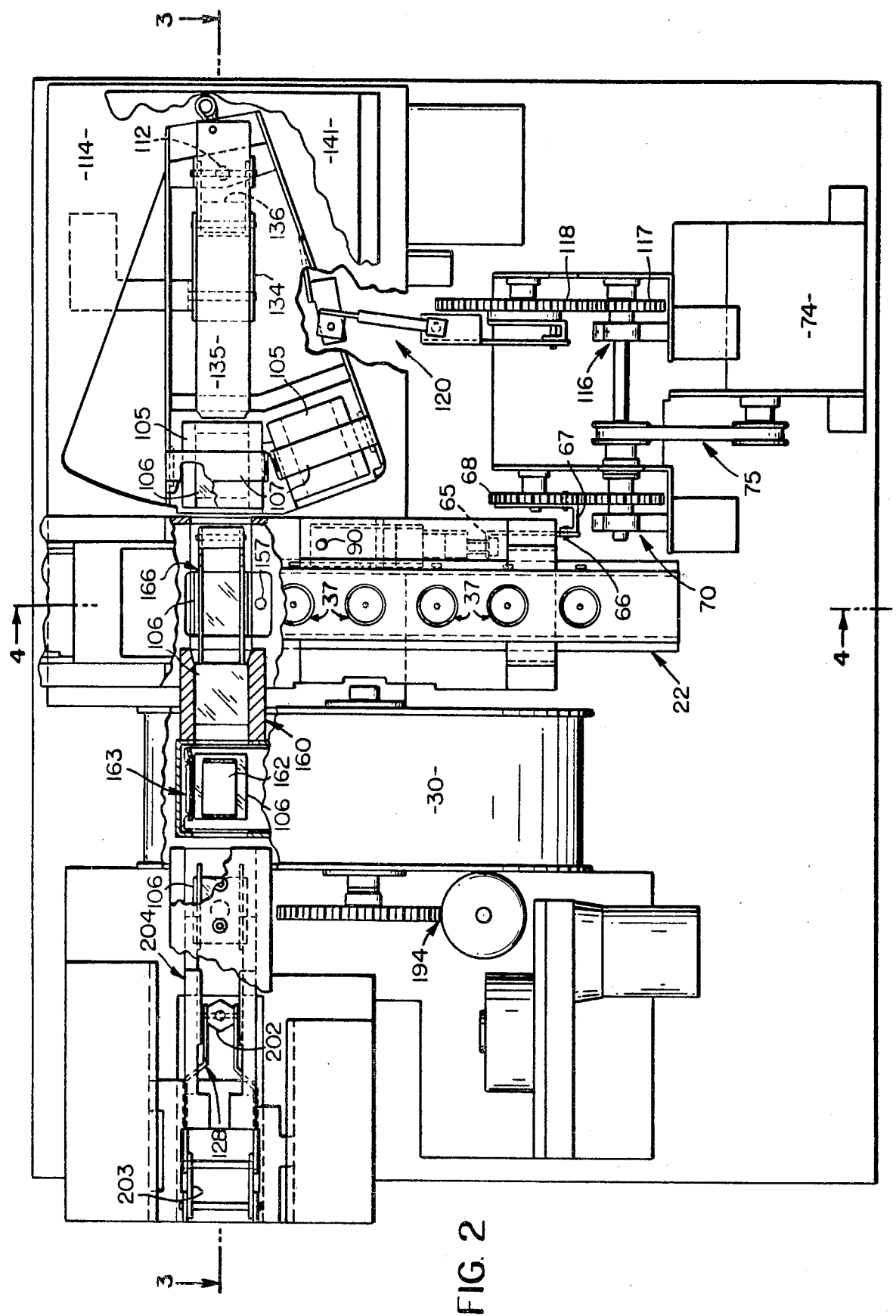
FIG. 2 is a top plan view of the analyzer.
Figure 3:
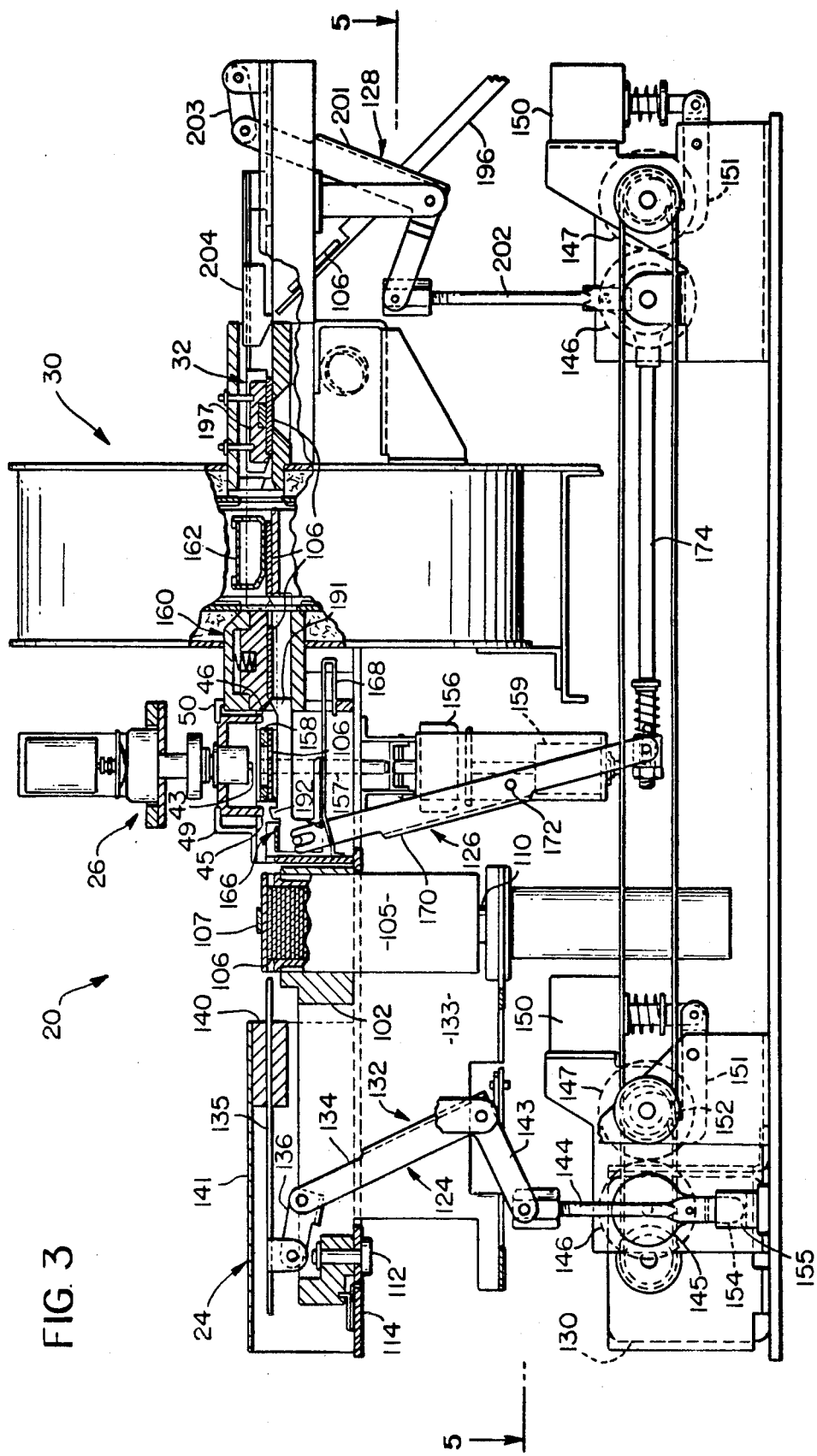
FIG. 3 is a sectional view, taken along the line 3—3 in FIG. 2.

In accordance with a preferred embodiment of the invention, there is shown in FIG. 1 a chemical analyzer 20 comprising a frame 14 which supports elements of the analyzer, including a sample tray 22, a reagent supply table 24, a metering device 26, an incubator 30, and analysis means 32. As shown in FIGS. 1–3, table 24, metering device 26, incubator 30, and analysis means 32 are supported closely adjacent each other in a side-by-side relationship. As will be discussed in more detail hereinafter, analyzer 20 is adapted to select a test slide from supply table 24 at a forward end of the analyzer, move the slide rearwardly to metering device 26 where a drop of biological fluid is placed thereon, deposit the slide in incubator 30, move the slide to analysis means 32 where a radiometric reading of the slide is taken, and then move the slide into a discharge chute (FIG. 3) at a rear end of the analyzer.

Figure 4:
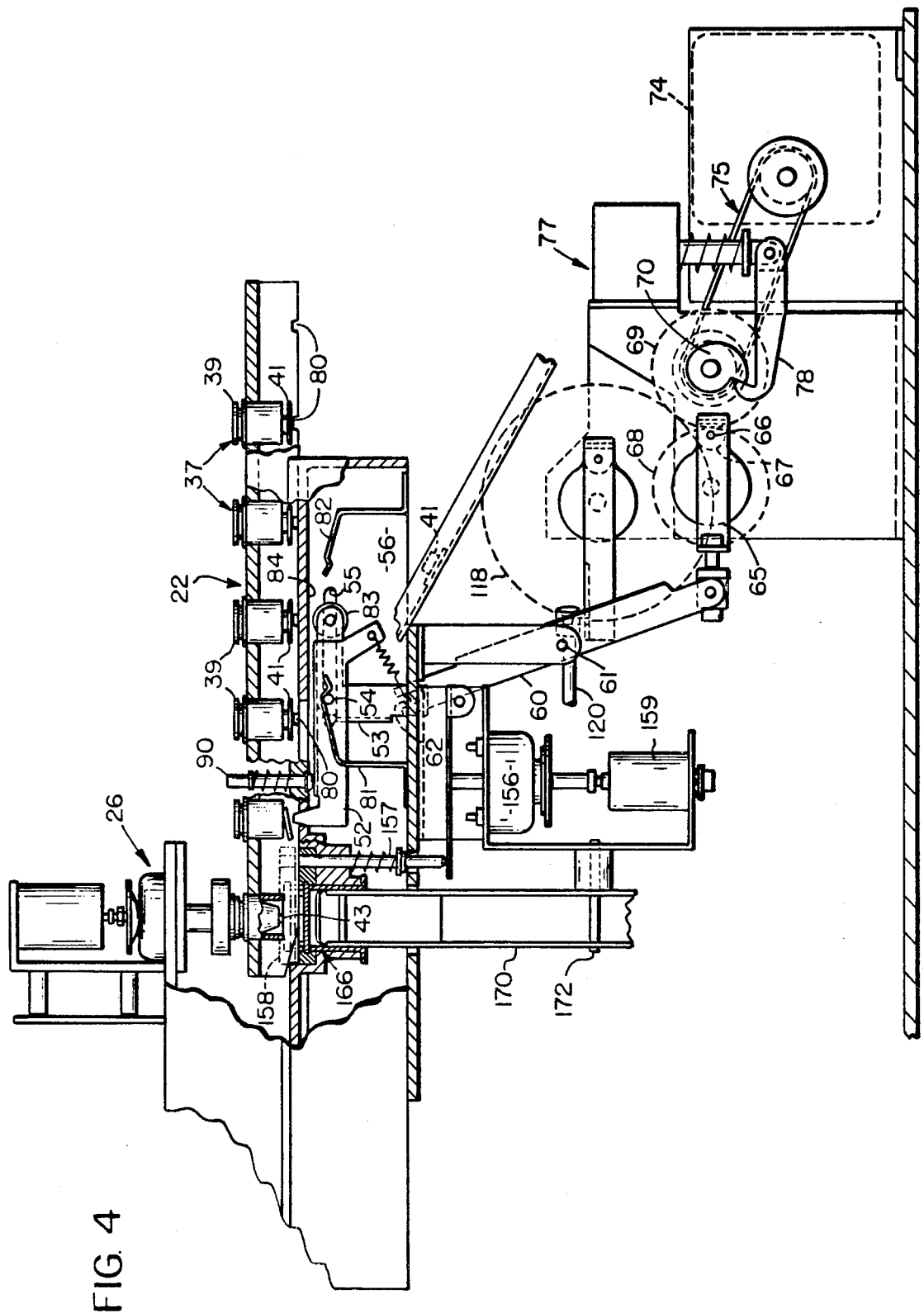
FIG. 4 is a sectional view, taken along the line 4—4 in FIG. 2.

With reference to FIGS. 2 and 4, biological fluids to be tested are poured into sample cups 37 which are loaded into sample tray 22. Each cup 37 is provided with a removable top cap 39 and a removable bottom cap 41 which covers a metering tip 43 in the cup; the metering operation will be explained in more detail later. Sample tray 22 is removably mounted on the analyzer in tracks 45, 46, and is held therein by means of brackets 49 and 50 (FIG. 3). Tray 22 is adapted to be moved along tracks 45, 46, to successively position cups 37 under metering device 26.

As shown in FIG. 4, movement of tray 22 is provided by a pawl 52 which is connected to an element 53 by means of a pin 54 which rides in a groove 55 in analyzer frame member 56. An arm 60, pivotally mounted at 61 and connected to element 53 at 62, serves to reciprocate pawl 52. Reciprocating motion is transmitted to arm 60 by means of a link 65 which is pinned at 66 to an eccentric 67 carried on a gear 68. Gear 68 is driven by a gear 69 connected to a one-revolution clutch 70. Clutch 70 receives power from a motor 74 through a belt connection 75. A solenoid 77 is adapted to release a pawl 78 to start operation of clutch 70.

Upon actuation of clutch 70, gear 68 will pass through one revolution. During the first one-half revolution, pawl 52 will be disengaged from a notch 80 in tray 22 and will be moved, from the position shown in FIG. 4, to the right to engage a new notch 80 in the tray 22. During the second one-half revolution of gear 68, pawl 52 will be moved back to the position shown in FIG. 4, thereby moving tray 22 the distance between two notches 80 and advancing a new cup 37 into the metering position. Springs 81 and 82 are provided to pivot pawl 52 out of a tray notch 80 at the initiation of a tray-advance cycle and to move pawl 52 back into a notch 80 just prior to the return stroke. Springs 81, 82 accomplish this function by releasably holding pin 54 at the start of each stroke of arm 60, thereby causing element 53 to pivot pawl 52, the direction of pivotal movement depending on the direction of movement of arm 60. A roller 83 carried on element 53 abuts against surface 84 on frame member 56 and limits pivotal movement of pawl 52 and element 53. A spring-loaded detent, not shown, is adapted to hold tray 22 in position when pawl 52 has been moved out of a notch 80. Tray 22 can be removed from the analyzer by depressing spring-loaded pin 90 to disengage pawl 52 from a notch 80, permitting the tray to be pulled out of the analyzer.

Reagents for use in the analyzer are carried on reagent supply table 24, shown in FIGS. 1–3. Table 24 comprises a pair of chambers 102 which are adapted to receive cartridges 105 each of which contains a stack of test slides 106 suitable for use in the apparatus of this invention. A highly preferred form of slide is described in Belgian Pat. No. 801,742, granted on Jan. 2, 1974. The slides disclosed in the Belgian patent are formed as a multi-layer element containing the necessary reagents for reaction with components of a biological fluid, such as blood serum, deposited thereon. Certain reactions colorimetrically produce a change in optical density which is sensed by a radiometer, the amount of light reflected from the element varying in accordance with the reaction and being indicative of the amount of a particular component present in the fluid.

The invention can also be used with other forms of test elements, as for example, the element disclosed in commonly-assigned U.S. Application, Ser. No. 687,725, entitled DEVICE AND METHOD FOR DETERMINING IONIC ACTIVITY OF COMPONENTS OF LIQUID DROPS, filed in the name of D. Hamblen et al. on May 19, 1976, and now U.S. Pat. No. 4,053,381. This application describes an element, or test slide, of the type which is used to potentiometrically designate the activity of ions in a liquid test solution by the use of electrodes.

With reference to FIGS. 2 and 3, each of the cartridges 105 is adapted to contain slides having the appropriate reagent incorporated therein for a particular test, such as a reagent for testing glucose in blood serum. Cartridges 105 are removably held in chambers 102 by means of pivotally mounted spring clips 107. A spring biased plunger 110 mounted on table 24 is adapted to engage the stack of slides through an opening, not shown, in cartridge 105 to bias the slides upwardly into a feed position.

Supply table 24 is pivotally mounted on a pin 112 fixed to a base plate 114 in frame 14. Table 24 is adapted to be moved, from a first position in which slides 106 can be fed from a cartridge in one of the chambers 102 to a second position in which slides can be fed from a cartridge in the other chamber 102, by a positioning means (see FIG. 2) which comprises a motor 74 operatively connected to a drive gear 117, a driven gear 118, and suitable linkage designated 120. The ratio of gears 117 and 118 is such that one revolution of gear 117 rotates gear 118 through one-half revolution, which serves to move supply table 24 sufficiently to change the cartridge located in the feed position.

With reference to FIG. 3, slides are fed from a cartridge 105 and transported through the various components of analyzer 20 by a slide handling means having a plurality of independently actuatable drive means which include an ejector mechanism 124, a forward transfer mechanism 126, and a rear transfer mechanism 128; each of these three mechanisms is adapted to be selectively coupled to a drive motor 130, as will be described in more detail hereinafter.

Ejector mechanism 124 comprises a bell crank 132 pivotally mounted to a frame member 133 and having a first leg 134 which is connected to a pusher member 135 through a link 136. Pusher member 135 is mounted for reciprocating movement in a bearing block 140 carried on a cover member 141. A second leg 143 of bell crank 132 is pinned to a connecting rod 144 which transmits power to bell crank 132. Rod 144 is adapted to pivot bell crank 132 through a limited arc which in turn causes pusher member 135 to reciprocate in and out of cartridge 105. As pusher member 135 moves into cartridge 105, it engages a slide 106 and moves it from the cartridge into a metering position directly under metering tip 43.

Connecting rod 144 is connected to an eccentric 145 carried on a gear 146. Eccentric 145 is connected to gear 146 through an overload detent device, not shown, which releases the eccentric from a driving connection with the gear when the drive torque exceeds a preselected value. Gear 146 is driven by a gear 147 connected to a drive shaft 148 through a one-revolution clutch 149. Clutch 149 is actuated by means of a solenoid 150 which lifts pawl 151 away from a ratchet 152 in clutch 149. Clutch 149 and solenoid 150 cooperate together to provide a means for selectively engaging drive motor 130 with ejector mechanism 24 to advance a slide into metering device 26 at the appropriate time in the analyzer cycle of operation.

Clutch 149 may be of any suitable type; however, one type which has been found to be particularly suitable is a spring clutch in which the gear 147 is connected to one end of a coil spring, not shown, which encircles drive shaft 148 and is connected at its other end to ratchet 152. Upon release of the pawl 151 the coil spring tightens on drive shaft 148 which causes gear 147 to rotate for one revolution. At the end of one revolution, pawl 151 again engages ratchet 152 to release the driving connection between the coil spring and drive shaft 148. As shown in FIG. 5, drive shaft 148 is connected to drive motor 130 through a belt means 153. As shown in FIG. 3, one end 154 of rod 144 is adapted to pass through a photodetector 155, of a known type, on each revolution; thus, if there is any blockage in the operation of the ejector means, a signal will be transmitted to an analyzer control panel, not shown.

When a slide 106 has been delivered to the metering position, a pendant drop of fluid is formed on tip 43 by metering device 26. For a description of the drop formation by metering device 26, reference is made to commonly-assigned U.S. Patent application Ser. No. 752,217, entitled METERING APPARATUS, filed in the name of Smith et al on Dec. 17, 1976. After a pendant drop is formed on tip 43, slide 106 is elevated to effect contact between the drop and the slide, causing the drop to be transferred to the slide. Slide 106 is elevated by means of a solenoid 156 which serves to raise a spring-loaded pin 157 fixed to a slide holding member 158. The slide is releasably held in member 158 by a leaf spring, not shown. When the drop has been transferred to slide 106, solenoid 156 is de-energized and pin 157 is returned to its starting position. A dashpot 159 is operative to regulate the rate of movement of slide 106 in the metering operation.

When fluid has been deposited on slide 106, forward transfer mechanism 126 is actuated to advance the slide from the metering position to a preheater 160 and the slide from preheater 160 into a slide holding member 162 on a rotor 163 of incubator 30. Slide holding member 162 is sufficiently flexible to receive and releasably hold a slide delivered to the incubator by transfer mechanism 126. An incubator of the type disclosed herein is described and claimed in commonly-assigned U.S. Pat. application No. 855,124, entitled INCUBATOR FOR CHEMICAL ANALYZER, filed in the name of Tersteeg et al. on Nov. 28, 1977.

Transfer mechanism 126 comprises an elongated element 166 having a first slide engaging means in the form of a pair of claws 191 and a second slide engaging means in the form of a pair of claws 192 generally in line with the first pair. Element 166 is slideably mounted on a flexible element 168 and is connected at one end to an arm 170 which is pivotally mounted to an analyzer frame member at 172. Power is transmitted to arm 170 through a connecting rod 174 which is adapted to be selectively coupled with a drive shaft 176 through gears 146, 147, and one-revolution clutch 149, in the same manner as described above for connecting rod 144. A drive belt 180 delivers power from shaft 148 to shaft 176. As shown in FIG. 3, claws 191, 192, on element 166 are tapered such that they are cammed under a slide when element 166 moves toward the forward end of the analyzer, and they move against a slide when element 166 moves toward the rear of the analyzer.

Incubator rotor 162 is driven by means of a worm-and-gear drive arrangement designated 194. (See FIG. 2.) When a slide 106 in the rotor has made one complete revolution, the slide is moved into the analysis means 32 by rear transfer mechanism 128 at the same time that a slide in the analysis means is moved to a discharge chute 196 by mechanism 128. A vertically movable element 197, which is biased against a slide by a spring, not shown, is adapted to releasably hold a slide in analysis means 32. Transfer mechanism 128 comprises a bell crank 201 which is oscillated by means of a connecting rod 202 through a one-revolution clutch 149 in a manner previously described for the forward transfer mechanism 126 and for the ejector mechanism 124. Bell crank 201 is connected through a link 203 to an element 204 which is adapted to simultaneously move a pair of slides in a manner generally similar to that described for element 166.

An important aspect of the invention is the particular arrangement for moving slides through analyzer 20. Supply table 24, metering device 26, incubator 30, and analysis means 32 are mounted in a side-by-side relationship to provide a generally linear slide path. With reference to FIG. 3, slides 106 are shown in section at operating positions in the slide path. Mechanisms 124, 126, and 128 of the slide handling means are independently actuatable to move a slide at the completion of a particular operation. The disclosed arrangement permits a substantial reduction in the time required to process a particular slide, and permits the movement of slides without the necessity for complex slide gripping means, such as suction cups or spring fingers.

In the operation of analyzer 20, a tray 22 containing cups 37 of fluid to be analyzed is placed on the analyzer with a cup 37 in the metering position, as shown in FIG. 4. Cartridges containing test slides for performing the two desired tests are mounted on supply table 24. With the sample cartridges 105 and the cups 37 in place, ejector means 124 is actuated to feed a slide into the metering position. A drop of serum is then formed on tip 43, and slide 106 is elevated to "touch-off" the drop. Slide 106 is then advanced by forward transfer mechanism 126 into the preheater 160, and then, after an appropriate length of time, into the incubator 30. The slide 106 is moved from incubator 30 into the analysis means 32 where a radiometric reading of the slide is taken. Subsequent to this reading, the slide is moved into discharge chute 196 which guides the slide to a disposal bin, not shown. Although the processing of a single slide has just been described, it will be understood that after an initial period of operation, slides will normally be at each of the operating positions, and the rotor of incubator 30 will be loaded with a plurality of slides.

A control system for analyzer 20 could include a computer, not shown, which may take any of the various forms known in the art that include programmable minicomputers and programmable microprocessors. The instructions and method of programming such computers is well known in the art, and thus, no further explanation is considered necessary. In the use of such a computer, input data including sample identification, calibration values, and desired tests for each sample would be keyed into the computer. Output signals from the computer would be utilized to provide input signals to the analyzer elements to control their operation at the appropriate time in the machine cycle. Results from analysis means 32 would be transmitted to the computer which would perform the necessary calculations, according to a stored program, to arrive at a concentration for a particular sample. This information, along with sample identification would then be transmitted to a display or printout device.

The invention has been defined in detail with reference to a certain preferred embodiment thereof, but it will be understood that variations and modifications can be effected within the spirit and scope of the invention.

What is claimed is:

1. Apparatus for measuring a characteristic of a fluid sample wherein the sample is deposited on a test slide which is analyzed after an appropriate period of incubation, said apparatus comprising:
    slide supply means;
    means adapted to receive a slide from said slide supply means at a metering position where a predetermined quantity of sample is deposited onto the slide;
    incubator means adapted to receive a slide bearing said quantity of sample;
    analysis means adapted to receive a slide from said incubator means;
    means for supporting each of said previously recited means relative to each other to define a path on which slides in contact therewith can be slideably moved through the apparatus; and
    slide handling means for moving a slide supported on said path through a plurality of locations on the path.

2. Apparatus, as defined in claim 1, wherein said slide handling means includes an ejector mechanism for removing a slide from said slide supply means and transfer means adapted to receive a slide from said ejector means.

3. Apparatus, as defined in claim 2, wherein said transfer means comprises a forward transfer mechanism for moving a slide from said metering position to a preheater in said incubator means and from said preheater to an incubator rotor, and a rear transfer mechanism for moving a slide from said rotor to said analysis means and from said analysis means to a discharge chute.

4. Apparatus, as defined in claim 3, wherein said ejector mechanism and said transfer mechanisms are driven from a single power source, and each of said mechanisms is selectively engageable with said power source.

5. Apparatus, as defined in claim 4, wherein said ejector mechanism comprises a pusher element, and each of said transfer mechanisms comprises a pair of slide engaging means.

6. Apparatus, as defined in claim 4, wherein said power source is connected to belt drive means, and each of said mechanisms is actuatable through one-revolution clutches adapted to be coupled to said belt drive means.

7. Apparatus, as defined in claim 2, wherein said supply means includes a supply table mounted for pivotable movement, said table having a plurality of chambers for receiving cartridges containing slides, and positioning means is adapted to move said table to locate a selected cartridge such that said ejector mechanism can feed a slide from the cartridge into the metering position.

8. An analyzer for measuring a characteristic of a fluid sample wherein the sample is deposited on a test slide which is analyzed after an appropriate period of incubation, said analyzer comprising:
    slide supply means;
    metering means adapted to receive and releasably hold a slide from said slide supply means, said metering means being further adapted to deposit a predetermined quantity of sample onto the slide;
    incubator means adapted to receive and releasably hold a slide bearing said quantity of sample;
    analysis means adapted to receive and releasably hold a slide from said incubator means;

means for supporting each of the previously recited means relative to each other to provide a generally linear slide path whereby slides can be slideably moved through the analyzer along said path; and slide handling means for sequentially applying a force to a slide supported on said path and in contact therewith to move the slide to a plurality of locations on the path.

9. Slide handling means for use in a chemical analyzer of the type in which a fluid is metered onto a test slide which is analyzed after an appropriate period of incubation, said slide handling means comprising:

a power source;

a plurality of independently actuatable drive means mounted for reciprocation, said drive means being adapted to engage the slide in a predetermined sequence to advance the slide through said analyzer; and means for selectively engaging each of said drive means with said power source.

10. Slide handling means, as recited in claim 9, wherein said means for selectively engaging each of said drive means comprises clutch means connected to each of said drive means, each of said clutch means being actuated by a solenoid.

11. Slide handling means, as recited in claim 10, wherein said power source comprises a motor adapted to be running continuously during the operation of said analyzer, and belt means transmits power from said motor to said clutch means.

12. Slide handling means, as recited in claim 9, wherein said drive means comprises an ejector mechanism for feeding a slide from a supply cartridge into metering means, a forward transfer mechanism for moving a slide from said metering means to a preheater and from the preheater to an incubator rotor, and a rear transfer mechanism for moving a slide from said incubator rotor to analysis means and from said analysis means to a discharge chute.

13. Slide handling means, as recited in claim 12, wherein each of said transfer mechanisms comprises two pairs of claws, and each pair of claws is adapted to engage and move a slide.

14. Slide handling means, as recited in claim 12, wherein each of said mechanisms includes a slideably mounted element which is adapted to engage and move a slide.

15. Apparatus for chemical analysis of a fluid sample wherein the sample is deposited on a test slide which is analzyed after incubation, including slide supply means, means adapted to receive a slide at a metering position where a predetermined quantity of sample is deposited on the slide, incubator means for receiving a slide bearing said quantity of sample, and analysis means for receiving a slide from the incubator means, the improvement wherein means provides a slide path which extends from said supply means through said metering position and the incubator means to the analysis means, said path being adapted to support a slide in contact therewith, and slide handling means is adapted to slideably move a slide on said path.

16. Apparatus for measuring a characteristic of a fluid sample wherein the sample is deposited on a test slide which is analyzed after an appropriate period of time, said apparatus comprising:

a plurality of apparatus elements, said elements being adapted to interact with the slide in a preselected sequence, said elements including metering means for depositing a predetermined quantity of sample on a slide in a metering position and analysis means for sensing a characteristic of the slide after a predetermined period of time;

means defining a slide path for movement of slides between said elements, said path being adapted to support slides in contact therewith for slidable movement thereon; and slide handling means for sequentially applying a force to a slide supported on said path to advance the slide past said elements.

17. Apparatus, as defined in claim 16, wherein said path is generally linear and extends through each of said elements.

18. Apparatus, as defined in claim 17, wherein said elements include slide supply means, and said slide handling means includes an ejector mechanism for removing a slide from said slide supply means and transfer means adapted to receive a slide from said ejector means.

19. Apparatus, as defined in claim 18, wherein said elements include incubator means having a preheater and a rotor, said transfer means comprises a forward transfer mechanism for moving a slide from said metering position to said preheater and from said preheater to said rotor, and a rear transfer mechanism for moving a slide from said rotor to said analysis means and from said analysis means to a discharge chute.

20. Apparatus, as defined in claim 16, wherein said slide handling means comprises a plurality of independently actuatable drive means, and means for selectively actuating said drive means.

* * * * *